United States Patent [19]  [11] 4,236,529
Little  [45] Dec. 2, 1980

[54] TINED LEAD

[75] Inventor: Richard L. Little, Minneapolis, Minn.

[73] Assignee: Daig Corporation, Minnetonka, Minn.

[21] Appl. No.: 13,129

[22] Filed: Feb. 21, 1979

[51] Int. Cl.³ .............................................. A61N 1/04
[52] U.S. Cl. ..................................... 128/785; 128/786
[58] Field of Search ............................... 128/784–786, 128/788, 419 P, 642

[56] References Cited

U.S. PATENT DOCUMENTS

| 3,533,403 | 10/1979 | Woodson | 128/419 P X |
| 3,749,101 | 7/1973 | Williamson | 128/419 P X |
| 4,030,508 | 6/1977 | Thalen | 128/419 P X |
| 4,135,518 | 1/1979 | Dutcher | 128/642 |

FOREIGN PATENT DOCUMENTS 423462 9/1974 U.S.S.R. ................................ 128/785

Primary Examiner—Lee S. Cohen
Attorney, Agent, or Firm—Clayton R. Johnson

[57] ABSTRACT

A tined lead that includes an insulated electrical conductor having one end electrically connectable to a pulse generator and an opposite end extending into one end portion of a metal electrode in electrically conductive relationship therewith, the opposite end portion of the electrode having a rounded tip for contacting body tissue, an axial bore through the tip surface to reduce the electrical conductive surface area of the tip and cross bores intersecting the axial bore remote from the tip, nonconductive, integrally joined plastic plugs filling said bores, and a nonconductive molded plastic member circumferentially surrounding the electrode, other than the tip, and the portion of the conductor that is connected to the electrode; the molded plastic member having a plurality of circumferentially spaced tines extending outwardly in a direction away from the tip. The tines are finned shaped and are flattened to be more flexible about axes parallel to the electrode axis than about axes perpendicular thereto.

14 Claims, 6 Drawing Figures

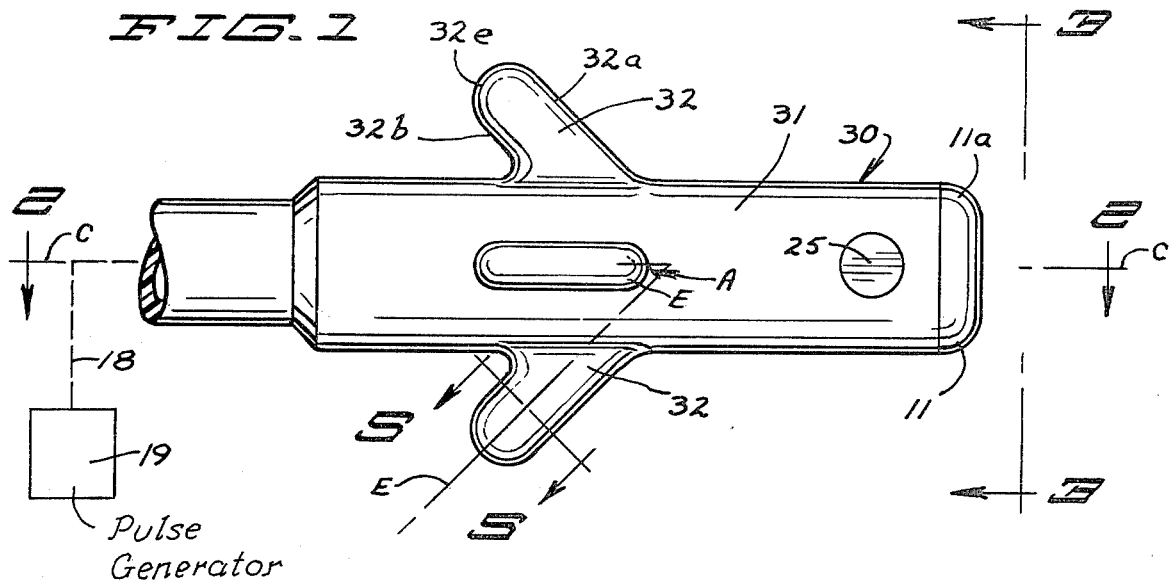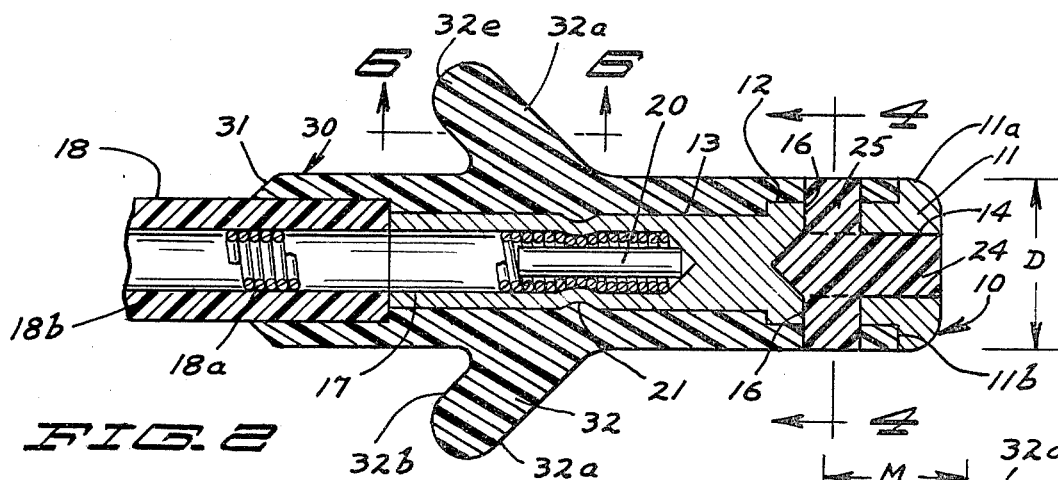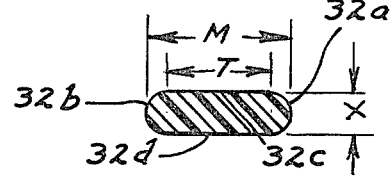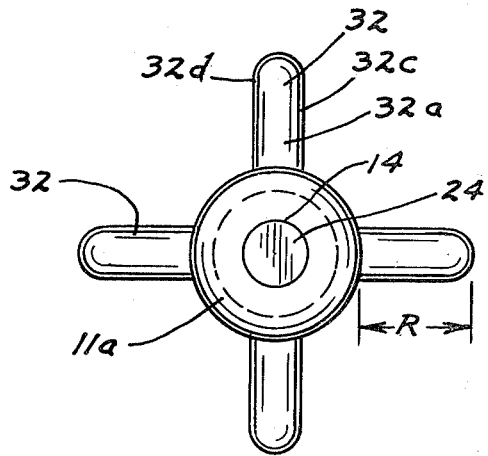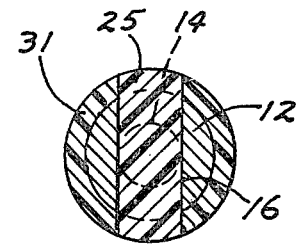

TINED LEAD

BACKGROUND OF THE INVENTION

A tined lead adapted for attachment to organ trabeculations, for example in a heart, to conduct electrical pulses to stimulate the tissue.

It is old to provide an electrode having a tip portion with an axial bore extending through the tip surface and into the reduced diameter portion of the electrode and fill the bore with silicone rubber. Also it is old to provide an axial bore in an electrode that is wider at a location axially remote from the tip surface than at its opening through the tip surface and fill such a bore with silicone rubber. However, problems encountered with such prior art electrodes include that one does not know if the bore is filled or how well the silicone rubber is anchored in the bore. Further, to drill a bore in an electrode that is narrower at the tip surface than it is at a location remote from the tip surface increases the expense of making the electrode.

Additionally, it is old to provide a lead that has tines that are circular in cross sections perpendicular to the directions that the tines extend away from the portions of the lead to which the tines are joined. However, with such prior art tined leads, in the event the lead is to be reset, in withdrawing the lead from the heart, the heart muscle may be damaged since the leads do not have much "give" while being withdrawn.

In order to minimize and/or overcome problems such as the above, this invention has been made.

SUMMARY OF THE INVENTION

A tined lead assembly that includes an electrode having a surface adapted to be in electrically conductive relationship to body tissue and a central axis and a plurality of inclined tines extending outwardly of the central axis and away from said surface, each of said tines being of a flattened configuration. When the electrode is provided with a tip having a tip surface that has an axial bore opening through the tip surface and a plastic plug filling the axial bore, it is preferred that there be provided a cross bore that intersects the axial bore and a plastic plug filling the cross bore and integrally joined to the plug in the axial bore.

One of the objects of this invention is to provide a tined lead that has tines of a new and novel configuration. Another object of this invention is to provide a lead for use in applying electrical stimulation to body tissue with new and novel circumferentially spaced tines that are more flexible in a direction of rotation about the lead electrode central axis than in an axial direction.

A further objective of this invention is to provide a lead electrode with new and novel means for anchoring a plastic plug in an axial bore that opens through the surface of a tip that is adapted to be in contact with body tissue.

BRIEF DESCRIPTION OF THE DRAWINGS

FIG. 1 is a side view of the distal end portion of the lead of this invention and diagrammatically shows the lead connected to a pulse generator;

FIG. 2 is a longitudinal cross sectional view of the distal end portion of the lead, said view being generally taken along the line and in the direction of the arrows 2—2 of FIG. 1;

FIG. 3 is an end view generally taken along the line and in the direction of the arrows 3—3 of FIG. 1;

FIG. 4 is a transverse cross sectional view generally taken along the line and in the direction of the arrows 4—4 of FIG. 2 to more fully show the cross plugs;

FIG. 5 is a transverse cross sectional view generally taken along the line and in the direction of the arrows 5—5 of FIG. 1 to more clearly show the flattened configuration of a tine; and FIG. 6 is a transverse cross sectional view taken parallel to the electrode central axis, said view being generally taken along the line and in the direction of the arrows 6—6 of FIG. 2.

Referring now to the drawings, the tined lead of this invention includes an axially elongated, electrically conductive, metal electrode, generally designated 10, that has a tip 11 integrally joined to one axial end of an intermediate diameter portion 12. The opposite end of portion 12 is integrally joined to an axially elongated reduced diameter portion 13. An axial bore 14 opens through the front tip surface 11a and extends through a substantial part of the intermediate diameter portion. The surface 11a is of a generally circular shape in axial spaced planes through the tip perpendicular to the central axis of the electrode and extends from outlet edge of bore 14 to the annular shoulder 11b at the juncture of the tip to the intermediate diameter portion. Shoulder 11b is concentric to bore 14.

Further, surface 11a is rounded in the planes of the electrode central axis.

A cross bore 16 extends through the intermediate diameter portion 12 to open to bore 14 on diametrically opposite sides thereof. Advantageously, bore 16 is of about the same diameter as bore 14 and extends radially relative the electrode central axis.

The reduced diameter portion of the electrode is provided with an axially elongated bore 17 that opens through the end opposite the tip and terminates short of bore 14. An insulated electrical conductor 18 has one end portion of its axially elongated, electrically conductive coil spring 18a extended into bore 17, the opposite end portion being adapted to be electrically connected to a terminal of a pulse generator 19 that provides pulses for maintaining a desired rate of heart beats. A tubular layer of insulation 18b surrounds the coil except at its opposite end portions. Advantageously, the end portion of the coil extended into bore 17 is attached to the electrode by having a rod 20 located in the coil and the reduced diameter portion 13 crimped at circumferentially spaced locations 21 to retain the coil in electrically conductive relationship with the electrode.

A molded plastic plug 24 fills the bore 14 and is integrally joined to plastic plugs 25 that fill the cross bores 16. Advantageously, the plugs are made of silicone rubber. Preferably the plugs are of sufficient transparency that one can see the plugs are joined. Due to the provision of the cross bores and plugs 25, the plug 24 is firmly anchored in bore 14, and if the plastic is sufficiently clear or translucent, one can visually ascertain whether or not plugs 25 are joined to plug 14.

A tined member, generally designated 30, has a tubular portion 31 that surrounds the end portion of insulation layer 18b that is adjacent the electrode and extends into abutting relationship with tip shoulder 11b whereby surface 11a is left uncovered. A plurality of circumferentially spaced, fin shaped tines 32 have their radial inner ends integrally joined to the outer circumferential portions of tubular portion 31 intermediate the axially opposite ends of the tubular portion. Preferably the tines are equally circumferentially spaced from one another.

The tines are inclined to extend radially outwardly in a direction axially (rearwardly) away from the tip, the central axes of elongation of the tines intersecting the central axis C—C of the electrode at angles A. Angle A may be about 45°. Thus the angle of inclination of the front linear part of the front edge 32a of each tine with reference to the cylindrical portion 31 is an obtuse angle while the angle inclination of the rear linear part of the rear edge 32b is an acute angle. Further, in a plane perpendicular to the axis of elongation E—E that passes through the linear portions of edges 32a, 32b, each of the edges 32a, 32b is of a semi circular shape while the linear side surface portions 32c, 32d are generally parallel. As may be noted from FIG. 5, in the last mentioned plane the minimum spacing (dimension X) of edges 32c, 32d maybe greater or smaller than the minimum spacing between the front and rear edges 32a, 32b (dimension Y) that is in the same plane but substantially less than the maximum spacing of the front and rear edges (dimension Z) that is taken in said plane and parallel to the linear side surfaces 32c, 32d. Dimension X is thus taken perpendicular to dimensions Y and Z. As may be noted from FIG. 6, in a longitudinal plane parallel to the central axis of the electrode that passes through the linear parts of edges 32a, 32b, the dimension X is substantially less than dimension T of each of the side surfaces 32c, 32d (minimum dimension between edges 32a, 32b) that is taken in the last mentioned plane between edges 32a, 32b; while the maximum M taken in said plane and parallel to side edges 32c, 32d is more than twice that of dimension X. Thus, when the tines are surrounded by body tissue each tine more easily bends above axes parallel to both the electrode central axis and the side edges 32c, 32d than they do about axes perpendicular thereto.

The outer end portions 32e of the tines are rounded while inwardly of edges 32a, 32b and linear side surfaces 32c, 32d the tines are curved to their juncture with the cylindrical portion 31.

Due to the shape of the tine front and rear edges the tines may be moved axially past organ trabeculations more easily than they can be withdrawn if the moving forces are just in an axial direction. However, if the electrode is twisted (rotated about its central axis) at the same time an axial withdrawing force is applied, the tines bend whereby their outer edge portions 32e move more closely adjacent the outer circumferential surface of the cylinder portion 31 than said outer edge portions would be if no twisting force were applied. As a result less force is required to withdraw the lead from an implanted position in organ trabeculations where both a twisting and axial withdrawal force is applied than if only an axial withdrawal force is applied. Since the tine outer edge portions 32e move closer to the cylinder portion 31 and less force is required in withdrawing the lead from an organ trabeculation implanted position, less damage is done to the trabeculations in resetting the electrode than where a conventional tined electrode is used.

In making the lead of this invention the tined member may be mold casted after the formation of electrode bores 14, 16 and the filling thereof with plastic in which case the plugs 25 would terminate as a circumferential extension of the outer surface of intermediate diameter portion 12 and cylinder portion would have no openings with plugs extending therethrough; or the tined member may be mold casted on the electrode, then bore 14, 16 made with the bores 16 extending through portion 31 and thence the bores filled with plastic to provide the lead as illustrated in FIG. 2; or bores 14 and 16 formed in the electrode and the tined member and plugs mold casted at the same time.

The rod (or tube) 20 is positioned in the coil 18a and the electrode crimped prior to the tined member being formed on the electrode. However, it is to be understood an electric conductor other than a spring coil can be used and that the conductor can be electrically connected to the electrode other than as described herein.

As an example of one model of the invention, but not otherwise as a limitation thereof, dimension X may be 0.030 of an inch, dimension Z 0.050 of an inch, the maximum radial distance R that a tine extends away from the cylinder portion 31 0.076 of an inch and the outer diameter of the tip at shoulder 11b 0.110 of an inch (dimension D).

Desirably the plugs and tined member are made of a material such as silicone rubber.

Even though the lead described is unipolar, it is to be understood the fin shaped tines and the filled cross bore feature can be used on a bipolar electrode.

What is claimed is:
1. For a lead that conducts electrical pulses to body tissue, an electrode having a central axis, a rear end portion; and a tip having a front tip surface adapted to be placed in electrical conductive relationship to body tissue and tined means joined to the electrode for attachment to trabeculations to aid in retaining the tip in electrical conductive relationship to body tissue, the tined means including a tine inclined relative the electrode to extend outwardly therefrom in a direction from the tip surface toward the rear end portion, one dimension of the tine in a plane perpendicular to the direction of extension of the tine away from the electrode being substantially greater than a second dimension of the tine in the same plane that is at right angles to said one dimension, and a tubular portion surrounding the electrode and having a front end portion disposed adjacent the front tip surface and a rear end portion disposed adjacent the electrode rear end portion and more remote from the tip front surface than the tine, the tine being integrally joined to the tubular portion intermediate its front and rear end portions to extend outwardly thereof in a direction away from the tip surface.

2. The apparatus of claim 1 further characterized in that tine has first and second surface portions that are opposite and generally parallel to one another and a rounded front surface portion extending between the first and second surface portions.

3. The apparatus of claim 1 further characterized in that the electrode includes an axially elongated cylindrical portion rearwardly of the tip, and that the tubular portion is axially elongated, is mounted on the electrode and extends around the cylindrical portion.

4. The apparatus of claim 3 further characterized in that the tined means includes a second tine of substantially the same size and shape as the first mentioned tine, the second tine being joined to the tubular portion in substantial angular relationship to the first mentioned tine.

5. The apparatus of claim 3 further characterized in that the tine is of a flattened construction having a substantially greater flexibility in an angular direction about said central axis than in an axial direction.

6. The apparatus of claim 5 further characterized in that the tined means is made of an electrically insulating material.

7. The apparatus of claim 3 further characterized in that the electrode has an axially extending bore opening through the tip surface and a first cross bore opening through the electrode surface rearwardly of the tip surface and opening to the axial bore, and a plug of an electrical insulating material filling said bores.

8. The apparatus of claim 7 further characterized in that the electrode has a second cross bore aligned with the first cross bore, the cross bores being located axially intermediate the tip and the tine; and that said plug fills the second cross bore.

9. A lead for conducting electrical pulses to body tissue comprising an axially elongated electrode having a rear end portion, central axis, and a tip having a front tip surface adapted to be placed in electrical conductive relationship to the body tissue, tined means mounted on the electrode for contacting trabeculations to aid in retaining the tip in electrically conductive relationship to body tissue, the tined means including a tubular member surrounding the electrode at a location spaced from the tip front surface and having a front end portion and a rear end portion more remote from the tip surface than the front end portion, and a plurality of circumferentially spaced tines integrally joined to the tubular member intermediate its front and rear end portions and at the juncture to the tubular member being spaced from the tubular member front and rear end portions, the tines extending radially outwardly from the tubular member in a axial direction axially from the front end portion toward the rear end portion, each tine in a plane parallel to the central axis being of a greater dimension in an axial direction than a dimension thereof that is in a direction perpendicular to said axial direction, each tine having a rounded front surface and opposite flattened side surface portions extending radially away from the rounded front surface toward the rear end portion, and an insulated electrical conductor electrically connected to the electrode.

10. The lead of claim 9 further characterized in that the tines are finned shaped and extend radially outwardly of the tubular member and away from the tip at angles about 45° relative the central axis and that the dimension in direction parallel to the central axis is more than twice the dimension in a direction perpendicular thereto.

11. A lead for conducting electrical pulses to body tissue comprising a metal electrode having a central axis, a tip having a front tip surface adapted to be placed in electrical conductive relationship to the body surface, a first bore opening through the tip surface, a cylindrical portion having a rear end portion and a front end portion joined to the tip to provide a rearwardly facing annular shoulder, the cylindrical portion having an exterior portion, and a second bore opening to the first bore and through the cylindrical portion exterior portion rearwardly of the tip surface, electrical insulation material filling said bores, and an insulated electrical conductor electrically connected to the electrode.

12. The apparatus of claim 11 further characterized in that a third member is mounted on the electrode, the tined member having a tubular portion that surrounds the cylindrical portion and has one end abutting against said shoulder, and a plurality of circumferential spaced tines joined to the tubular portion and extending radially outwardly thereof in a rearward direction, the tines being fin shaped and having a maximum dimension in an axial direction generally parallel to the central axis that is greater than the maximum dimension thereof in a direction perpendicular to the direction of the axial dimension and the direction of extension of the tine away from the tubular portion.

13. The apparatus of claim 12 further characterized in that the electrode has a third bore that is radially aligned with the second bore and opens to the first bore and through the cylindrical portion exterior portion, the electrical insulating material filling the third bore portion and being of silicone rubber, that the first bore is axially elongated and that the annular shoulder is concentric to the first bore.

14. The apparatus of claim 11 further characterized in that a tubular portion of electrical insulating material extends around the cylindrical portion, the insulating material in the second bore being joined to the tubular portion.

* * * * *

UNITED STATES PATENT AND TRADEMARK OFFICE
CERTIFICATE OF CORRECTION

PATENT NO. : 4,236,529
DATED : December 2, 1980
INVENTOR(S) : Richard L. Little

It is certified that error appears in the above-identified patent and that said Letters Patent are hereby corrected as shown below:

Column 6, line 19, change "third" to --tined--.

Signed and Sealed this

Third Day of March 1981

[SEAL]

Attest:

RENE D. TEGTMEYER

Attesting Officer    Acting Commissioner of Patents and Trademarks